United States Patent [19]

Orser et al.

[11] Patent Number: 4,540,667

[45] Date of Patent: Sep. 10, 1985

[54] FLUORESCENT SIDEROPHORE GENES

[75] Inventors: Cindy Orser; Joyce Loper, both of Berkeley; Nickolas Panopoulos, Oakland; Steven Lindow, Berkeley; Milton N. Schroth, Orinda, all of Calif.

[73] Assignee: The Regents of the University of California, Berkeley, Calif.

[21] Appl. No.: 433,606

[22] Filed: Oct. 12, 1982

[51] Int. Cl.³ .................. C12N 15/00; C12N 1/20; C12N 1/00; A01N 33/02; C05F 11/08
[52] U.S. Cl. .................. 435/172.3; 435/253; 435/317; 935/29; 935/60; 935/73; 71/79; 71/121; 71/6
[58] Field of Search ............ 435/172, 253, 317, 172.3; 536/27

[56] References Cited

U.S. PATENT DOCUMENTS 3,819,482  6/1974  Vidaver et al. .................. 435/91

OTHER PUBLICATIONS

Grosweld et al., Gene 13, pp. 227–237, 4–1981.
Clarke et al., Genetics and Biochemistry of Pseudomones, John Wiley & Sons, p. 31, (1975).

*Primary Examiner*—Alvin E. Tanenholtz
*Attorney, Agent, or Firm*—Bertram I. Rowland

[57] ABSTRACT

DNA sequences encoding for plant growth promotant activity have been isolated and introduced into microorganisms. The modified organisms are able to confer plant growth promotant activity analogous to that of the DNA source host. Such modified hosts find use in promoting the growth of root crops by innoculating the rhizosphere with such microorganisms.

*E. coli* HB101 (pS FL-1) was deposited at the A.T.C.C. on Oct. 8, 1982, and granted accession no. 39206.

9 Claims, No Drawings

FLUORESCENT SIDEROPHORE GENES

BACKGROUND OF THE INVENTION

1. Field of the Invention

Genetic evolution has afforded an extraordinary array of biological capabilities in nature. Various organisms and cells achieve these different functions by producing a wide variety of proteins, many of which can in turn produce a wide variety of non-proteinaceous molecules. These naturally occurring compounds can interact to modify their environment in countless ways.

It is known that certain soil microorganisms are beneficial to plant growth through the production of growth hormones, antibiotic substances which kill harmful soil microorganisms, and by aiding in the uptake of nutrients by plants. In particular, it has been found that certain fluorescent strains of the genus Pseudomonas enhance root crop production through the production of fluorescent siderophores which confer a competitive advantage on the Pseudomonas and inhibit the growth of competing deleterious microorganisms.

Siderophores are low molecular weight compounds which are capable of sequestering or chelating iron ($Fe^{+3}$) and acting as transport agents in supplying iron to the microorganism which produce them. While virtually all aerobic and facultative anaerobic microorganisms are able to produce siderophores under low iron stress, fluorescent pseudomonads produce particularly effective siderophores which act to reduce the availability of iron to other microorganisms resulting in the inhibition of disease-inducing microorganisms.

It would therefore be desirable to be able to confer on certain beneficial microorganisms the ability to preferentially compete for growth with other deleterious microorganisms in the root sphere (rhizosphere) of root crops such as potatoes, radishes, sugar beets, and the like. In particular, it would be desirable to be able to enhance the siderophore-producing capability of microorganisms which already display plant growth promoting activity.

2. Description of the Prior Art

A number of papers have been published concerning the ability of specific strains of fluorescent Pseudomonas to produce fluorescent siderophores and enhance the growth of certain root crops. See, for example, Kloepper and Schroth (1981), *Phytopathology* 71:1020–1023; Kloepper, et al. (1980) *Curr Microbiol.*, 4:317–320; and Kloepper, et al. (1980) *Nature*, 286:885–886. The structure of ferric pseudobactin, a siderophore obtained from a particular strain of fluorescent Pseudomonas, has been determined by Teintze, et al. (1981) *Biochemistry*, 20:6446–6457. Other articles of interest include Meyer and Abdallah (1978) *J. Gen. Microbiol.*, 107:319–328; Meyer and Hornsperger (1978) *J. Gen. Microbiol.*, 107:329–331; and Misaghi, et al. (1982) *Phytopathology*, 72:33–36.

SUMMARY OF THE INVENTION

DNA sequences encoding for substances which confer enhanced plant growth promotant activity on a microorganism are provided. The DNA sequences can be cloned in a host foreign to the source of the DNA and are capable of imparting plant growth promotant activity to such hosts as well as enhancing such activity in the source host itself. DNA sequences, vectors and transformants are described.

DESCRIPTION OF THE SPECIFIC EMBODIMENTS

The subject invention provides for the isolation and utilization of DNA segments encoding for plant growth promotant activity (PGPA). By inserting such DNA segments onto an appropriate vector, PGPA can be conferred upon a wide variety of hosts by introducing the vector according to conventional techniques. The vector may be a plasmid, phage, or other self-replicating extrachromosomal element which may be used for conjugation, transformation, transduction, or transfection of the microorganism host. The host may then be grown and cloned, and PGPA+ clones isolated. The resulting growth promotant microorganisms or subcellular portions or extracts derived therefrom, may be used to treat the rhizosphere of various root crops in order to suppress certain root crop diseases and promote the growth of the plant.

In particular, the DNA segments encode for the production of chelating agents which sequester limited multivalent inorganic cations in the soil which are essential nutrients for growth. More particularly, the DNA segments encode for the production of fluorescent siderophores which are capable of chelating $Fe^{+3}$. By introducing the subject DNA sequences to a host, the host is able to preferentially scavenge the available $Fe^{+3}$ in the soil, depriving other deleterious microorganisms in the soil of this essential nutrient. The deleterious microorganisms will generally either not produce siderophores, produce lesser quantities of siderophores, or produce siderophores having a lesser affinity for iron than the fluorescent siderophores.

The DNA sequence of interest will be about 20 kbp in length, or less, usually being greater than about 15 bp, more usually greater than 30 bp. The exact length of the sequence is not critical so long as, when introduced to an appropriate host, the PGPA is expressed.

In order to obtain a DNA sequence encoding for PGPA, a microorganism known to provide for PGPA can be employed. Conveniently, various species of Pseudomonas, such as *syringae, fluorscens,* and *putida,* may be employed as a source for the preparation of a gene library, either by random fragmentation of the genome or by synthesis of cDNA from mRNA.

Various restriction enzymes may be employed which provide for segments of up to 25 kbp by complete or incomplete digestion of the source genome. These fragments may then be cloned. Various vectors may be employed depending on the size of the fragment, the nature of the host, and the like. Plasmids, phages, and cosmids can be emloyed which allow for insertion of fragments from the genomic library as functional self-replicating extrachromosomal elements in the host. Such vectors should have convenient restriction sites which allow for insertion of the genomic library fragments. Desirably, the vectors should provide a means for selection and/or screening, typically through antibiotic selection, packaging requirements, inactivation of a gene, or other means.

Of particular interest for cloning is a cosmid vector, more particularly pLAFR1, which has a unique EcoRI site. This vector is a derivative of the vector pRK290 ($Tc^r$) that contains the cos sites of phage λ for in vitro packaging. It is a broad host range oligocopy vector, having the unique EcoRI site outside Tc gene. The vector pLAFR1 is particularly useful because it selects by packaging for inserts of about 20 kb±10 kb in length.

The vector is described by Friedman, et al. (1982) Gene Vol. 18 pages 289-296.

While the pLAFR1 plasmid does not provide for selection or screening based on insertional inactivation, the DNA sequences themselves will often provide a convenient selection technique. The substances produced by *P. syringae, P. fluorescens,* and *P. putida,* are fluorescent. By subcloning Tc+ colonies in a nonfluorescent host capable of expression, recombinant vectors may be selected based on their fluorescence.

Preparation of a cDNA gene library is accomplished by first isolating the mRNA fraction from the source microorganism. Care should be take to inactivate the RNases, typically by treatment with $BaSO_4-$ ribonucleoside complexes. After extracting the total RNA, the mRNA can be separated using a poly(U) or poly(T) chromatography medium which is specific for the poly(A) tail. The cDNA gene library can then be prepared using reverse transcriptase in the well known manner.

After cloning and screening, the DNA sequence of interest will be introduced into a soil microorganism for eventual population of the rhizosphere of the crop being treated. While it will sometimes be possible to introduce the cloning vector directly, it will often be necessary to excise the DNA sequence and insert it onto a vector which is compatible with the contemplated host microorganism.

The DNA sequence encoding for PGPA may be introduced into a wide variety of microorganisms capable of populating the rhizosphere of the various root crops, in particular bacteria and fungi. The choice of host will depend on the availability of a compatible vector, the purpose for introducing the PGPA into the host, and the manner in which the host is to be used. It is preferred to employ hosts which are PGPA+, in particular hosts in which the wild type produces fluorescent siderophores capable of imparting PGPA, such as *P.fluorescens, P.putida* and *P.syringae.* In the latter case, introduction of multiple copies of the DNA sequence will enhance the PGPA through the greater production of siderophores.

Depending upon the nature of the vector, various techniques may be used for introducing the vector carrying the DNA insert into the host. Transformation can be achieved in the conventional manner employing calcium precipitated DNA in an appropriate solvent. Transfection may be achieved by contacting the microorganisms with a modified virus, or its DNA in a nutrient medium. Transduction of the microorganisms occurs upon integration of the sequence into the genome. Conjugation can also be employed, where the plasmid is introduced into one organism, which may then transfer the plasmid to a different organism either being capable of mobilization by itself or in conjunction with a mobilizing plasmid. It is particularly desirable that the vector be non-self-transmissible to prevent transformation of deleterious microorganisms. Preferably, the DNA sequence will be integrated into the chromosome of any host which is introduced into the soil.

For Pseudomona hosts, derivatives of plasmid RSF1010 such as pKT212 and pKT214 are particularly useful as vectors. The DNA sequences of interest can be inserted at unique Bam HI and Bgl II site, and selection made based on the loss of $Tc^r$.

In isolating the organisms receiving the DNA sequences of interest, it is desirable to use a PGPA− organism, whereby a resulting clone which is shown to be PGPA+ is likely to have received a recombinant vector in the cloning. Moreover, when cloning in a nonfluorescent host capable of expressing the fluorescent gene product, selection can be made based on the fluorescent phenotype. Conveniently, the clones can be screened using a simple technique where colonies plated on an appropriate solid nutrient media are exposed with long-wave ultraviolet light (366 nm) which causes colonies expressing the recombinant gene product to fluoresce.

The modified microorganisms of the present invention may be utilized effectively in diverse formulations, including agronomically-acceptable adjuvants and carriers normally employed for facilitating the dispersion of active ingredients for agricultural applications. The precise formulation, dosage, mode of application and other variables are chosen to enhance the PGPA in any given application. Thus, the previously described modified microorganisms may be formulated as a suspension or a dispersion, an aqeous or non-aqeous medium, as a dust, as a wetable powder, as an emulsifiable concentrate, as a granule, or as any of several known types of formulations, depending on the desired mode of application. These compositions may be applied as sprays, dusts or granules to the seeds, seed pieces, roots, plants, soil, or planting site at which activity is desired. Such compositions are discussed in detail in copending application Ser. No. 404,103.

The following examples illustrate the isolation of the siderophore gene(s) and are not intended to limit the invention in any way.

EXPERIMENTAL

1. Construction of the DNA Library

The DNA from two fluorescent, siderophorebearing *Pseudomonas syringae* strains designated 31R1 and Cit7 was extracted, purified by two cycles of CsCl-ethidium bromide density gradient centrifugation, and dialyzed against appropriate buffers. The DNA was partially digested with Eco RI and fractionated by sucrose gradient centrifugation in 5-25% neutral sucrose. The partial digestion employed 0.3 units Eco RI per 1 µg DNA following the directions of the supplier (Bethesda Research Laboratories, MD) and the reaction stopped after 0.5 hr by heating at 65~ C. for three minutes. Fractions from the sucrose gradient were analyzed by agarose gel electrophoresis and those rich in fragments in the 18-25 kbp range were pooled, enriched by ethanol precipitation, and ligated to the cosmid vector pLAFR1 (Friedman, et al. (1982) Gene Vol. 18 pages 289-296, supplied by S. Long, Stanford, Calif.) previously linearized with Eco RI.

The cosmid pLAFR1 is a derivative of the plasmid pRK290 ($Tc^r$) that contains the cos site of phage lambda for in vitro packaging. pLAFR1 includes a single Eco RI insertional site (outside the $TC^r$ gene) and selects for inserts of about 20 kbp in length.

2. Derivation of *P. syringae* 31R1-26

A nonfluorescent mutant (designated 31R1-26) was derived from *P. syringae* 31R1 by chemical mutagenesis utilizing ethylene methane sulfonate (EMS). Strain 31R1 was grown in King's B broth overnight, 0.2 ml seeded into 10 ml fresh King's B broth, and grown for four hours to assure log phase growth. Five percent EMS was added to broth, mixed well, and incubated with shaking at 25~ C. for twenty minutes. Cells were then washed two times, resuspended in an equal volume of King's B broth, and placed back in the incubator for two hours. Segregated cells were then plated on King's B agar at cell densities of 30–50 colony-forming units/plate. After two days of incubation at 25° C., fluorescent colonies were identified by irradiation of plates with long-wave ultraviolet light (366 nm). The nonfluorescent mutant 31R1-26 was detected by observing its lack of fluorescence when irradiated with UV light.

To demonstrate that strain 31R1-26 was deficient in siderophore production, an iron-chelating compound (ethylene diamine dihydroxyphenyl acetic acid, 200 ppm) was added to the King's B agar to produce an iron-deficient medium. Strain 31R1, which produces a siderophore, was able to grow on the iron-deficient medium, while nonfluorescent mutant strain 31R1-26 was not. The inability of strain 31R1-26 to grow on iron-deficient medium was reversed upon addition of $10^{-4}$ M $FeCl_3$, confirming that iron starvation was responsible for the lack of growth.

Ligation of the DNA fragments in pLAFR1 was achieved using T4 DNA ligase following the supplier's directions (Bethesda Research Laboratories, MD). A high ratio of foreign DNA to linearized pLAFR1 was employed to minimize dimerization of the vector. About 3–4 μg of P. syringae DNA fragments were used per 1 μg of linearized pLAFR1. The ligation reaction was carried out in an appropriately buffered 10 μl volume that is heated at 65° C. for 5 minutes, 30 minutes at 42° C., followed by two hours at room temperature. ATP was then added to a concentration of 1 mM; 1 unit of T4 DNA ligase was added; and the ligation mixture was incubated at 12° C. overnight.

In vitro packaging was in accordance with the procedure described by Hohn, M. (In vitro Packaging of λ and Cosmid DNA, Wu, ed., Methods in Enzymology, vol. 68, Academic Press, New York, pages 299–309, 1979). Approximately 30 μl freeze-thaw (λ heads) and 20 μl sonicate (λ tails) extracts were combined with 2 μl, 1M ATP and 5 μl ligated DNA, and the resulting mixture incubated for one hour at room temperature and adjusted to 10 mM $MgCl_2$, 10 mM TRIS buffer, pH 7.6.

For transduction, 0.1 ml of the phage stock was mixed with 0.5 ml of E. coli HB101 cells grown to mid-log phase ($10^7$–$10^8$ cells/ml) in Luria broth supplemented with 0.4% maltose and incubated for one hour at 37° C. Two ml Luria broth was added, and the cells grown for 1.5–2.0 hours at 37° C. Transductants were selected on Luria agar supplemented with 10 mg/ml tetracycline (pLAFR1 confers resistance to the antibiotic).

3. Selection of Recombinant Plasmids Having Siderophore Gene(s)

Recombinant pLAFR1 plasmids conferring the fluorescent phenotype were selected by mating the transduced HB101 clones with the nonfluorescent mutant 31R1-26. Selection can then be made based on the acquired fluorescent phenotype. pLAFR1 is nonconjugative but mobilizable by the conjugative helper plasmid pRK2013.

First, single en masse matings of the HB101 (pLAFR-1—P. syringae) libraries with the nonfluorescent 31R1-26 mutant yielded a low frequency of complemented fluorescent transconjugants. These fluorescent transconjugants were able to grow on media containing 200 ppm EDDA, as indicated in Table I. However, repeated attempts to isolate the recombinant pLAFR1 plasmid from these transconjugates were unsuccessful.

Second, individual clones of the HB101 (pLAFR-1—P. syringae) library stored in microtiter plates were utilized as donors in 718 separate triparental matings with HB101 (pRK2013) and the nonfluorescent mutant 31R1-26. Two of the 718 separate conjugations resulted in transconjugants which were then fluorescent. Again, repeated attempts to isolate the recombinant plasmid from these transconjugants were unsuccessful, indicating that the cloned fragment complementing this genetic lesion may be incorporated into chromosomal DNA of the transconjugant clone.

The pLAFR1 recombinant plasmids were isolated from both HB101 clones which resulted in fluorescent transconjugants. These recombinant plasmids were designated pS FL-1 and pC FL-1. EcoRI digestion of both plasmids indicated that they were structurally identical and are probably duplicate clones which had been separately stored.

TABLE I

COMPLEMENTATION OF NONFLUORESCENT MUTANT OF *PSEUDOMONAS SYRINGAE* WITH CLONED DNA FRAGMENT

|  | Fluorescence | Growth on King's B | |
|---|---|---|---|
|  |  | EDDA (200 ppm) | EDDA + $10^{-6}$ M $FeCl_3$ |
| P. syringae 31R1 | + | + | + |
| P. syringae Cit 7 | + | + | + |
| P. syringae 31R1-26 | − | − | + |
| P. syringae 31R1-26 (pS FL-1) | + | + | + |
| P. syringae 31R1-26 (pC FL-1) | + | + | + |

It is apparent from the above results that PGPA can be transferred to hosts which have not previously had this capability. Moreover, the introduction of said DNA fragments into PGPA+ hosts to obtain increased expression of PGPA products through the use of a multiple copy vector is also possible. Thus, organisms capable of colonizing a wide variety of soil conditions can be modified so as to provide for PGPA in new environments and/or with higher efficiency.

Although the foregoing invention has been described in some detail by way of illustration and example for purposes of clarity and understanding, it will be obvious that certain changes and modifications may be practiced within the scope of the appended claims.

What is claimed is:

1. A rhizosphere inhabiting bacterial microorganism having enhanced ability to produce a fluorescent siderophore capable of sequestering $Fe^{+3}$ as a result of in vitro introduction into said microorganism, or into a parent of said microorganism, of a DNA sequence encoding for said siderophone which is expressed by a gene present in pS FL-1 (A.T.C.C. Accession No. 39206).

2. A microorganism according to claim 1, wherein said DNA sequence is incorporated on an extrachromosomal element.

3. A microorganism according to claim 1, wherein said DNA sequence is integrated into the chromosome.

4. A microorganism according to claim 1, wherein the microorganism was previously incompetent to produce siderophores.

5. A microorganism according to claim 1, wherein the microorganism was previously competent to produce siderophores.

6. A method for conferring on a bacterial host the ability to produce a fluorescent siderophore capable of sequestering $Fe^{+3}$, said method comprising:
  screening a gene library obtained from a fluorescent strain of Pseudomonas to obtain a DNA sequence which encodes for said siderophore, wherein said siderophore is encoded for by a DNA sequence present in pS FL-1 (A.T.C.C. Accession No. 39206);
  incorporating said DNA sequence onto a vector capable of replication and expression in the host; and
  introducing the vector into the host.

7. A method as in claim 6, wherein the vector is incorporated into the host genome.

8. A method as in claim 6, wherein the vector replicates independently of the host genome.

9. pS FL-1.

* * * * *